(12) United States Patent
Kruse et al.

(10) Patent No.: US 10,736,037 B2
(45) Date of Patent: Aug. 4, 2020

(54) METHODS OF WIRELESS COMMUNICATION IN AN INFUSION PUMP SYSTEM

(71) Applicant: Tandem Diabetes Care, Inc., San Diego, CA (US)

(72) Inventors: Geoffrey A. Kruse, San Diego, CA (US); Michael Michaud, San Diego, CA (US)

(73) Assignee: Tandem Diabetes Care, Inc., San Diego, CA (US)

( * ) Notice: Subject to any disclaimer, the term of this patent is extended or adjusted under 35 U.S.C. 154(b) by 0 days.

(21) Appl. No.: 16/725,278

(22) Filed: Dec. 23, 2019

(65) Prior Publication Data

US 2020/0213946 A1 Jul. 2, 2020

Related U.S. Application Data

(60) Provisional application No. 62/784,949, filed on Dec. 26, 2018.

(51) Int. Cl.
| | | |
|---|---|---|
| *H04M 3/00* | (2006.01) | |
| *H04W 52/02* | (2009.01) | |
| *A61M 5/172* | (2006.01) | |
| *H04M 1/725* | (2006.01) | |

(52) U.S. Cl.
CPC ........ *H04W 52/0229* (2013.01); *A61M 5/172* (2013.01); *A61M 5/1723* (2013.01); *H04M 1/7253* (2013.01); *A61M 2205/3561* (2013.01); *A61M 2205/3584* (2013.01); *A61M 2205/50* (2013.01); *A61M 2205/505* (2013.01); *A61M 2205/702* (2013.01); *A61M 2205/8212* (2013.01); *A61M 2230/201* (2013.01)

(58) Field of Classification Search
CPC ........... H04W 52/0229; H04M 1/7253; A61M 5/172; A61M 5/1723; A61M 1/7253; A61M 2205/3561; A61M 2205/3584; A61M 2205/50; A61M 2205/505; A61M 2205/702; A61M 2205/8212; A61M 2230/201
USPC .............................. 455/420, 445, 418, 550.1
See application file for complete search history.

(56) References Cited

U.S. PATENT DOCUMENTS

| | | |
|---|---|---|
| 6,768,425 B2 | 7/2004 | Flaherty et al. |
| 6,958,691 B1 | 10/2005 | Anderson et al. |
| 7,156,808 B2 | 1/2007 | Quy |
| 7,181,505 B2 | 2/2007 | Haller et al. |
| 7,347,836 B2 | 3/2008 | Peterson et al. |
| 7,654,976 B2 | 2/2010 | Peterson et al. |
| 7,779,183 B2 | 8/2010 | Koehler et al. |

(Continued)

*Primary Examiner* — Danh C Le
(74) *Attorney, Agent, or Firm* — Patterson Thuente Pedersen, Inc.

(57) ABSTRACT

Disclosed herein are methods for establishing communication protocols between wireless devices in infusion pump systems. Infusion pump systems can include a number of components capable of wireless communication with one or more other components including an infusion pump, a continuous glucose monitoring (CGM) system, a smartphone or other multi-purpose consumer electronic device and/or a dedicated remote controller for the infusion pump. Communications among these devices can be coordinated to increase efficiency and conserve battery power.

10 Claims, 12 Drawing Sheets

(56) References Cited

U.S. PATENT DOCUMENTS

| | | | |
|---|---|---|---|
| 7,931,613 B2 | 4/2011 | Haueter et al. | |
| 7,991,625 B2 | 8/2011 | Rosenfeld | |
| 8,025,634 B1 | 9/2011 | Moubayed et al. | |
| 8,095,123 B2 | 1/2012 | Gray | |
| 8,117,481 B2 | 2/2012 | Anselmi et al. | |
| 8,126,728 B2 | 2/2012 | Dicks et al. | |
| 8,126,730 B2 | 2/2012 | Dicks et al. | |
| 8,140,356 B2 | 3/2012 | Dicks et al. | |
| 8,155,982 B2 | 4/2012 | Dicks et al. | |
| 8,172,082 B2 | 5/2012 | Edwards et al. | |
| 8,236,242 B2 | 8/2012 | Drucker et al. | |
| 8,287,495 B2 | 10/2012 | Michaud et al. | |
| 8,372,351 B2 | 2/2013 | Ow-Wing | |
| 8,454,554 B2 | 6/2013 | Reinke | |
| 8,478,237 B1 * | 7/2013 | Stenta | H04M 1/67 340/438 |
| 8,533,475 B2 | 9/2013 | Frikart | |
| 8,573,027 B2 | 11/2013 | Rosinko et al. | |
| 8,952,794 B2 | 2/2015 | Blomquist | |
| 8,986,253 B2 | 3/2015 | DiPerna | |
| 9,173,992 B2 | 11/2015 | Bengtsson | |
| 9,381,297 B2 | 7/2016 | Brown et al. | |
| 9,474,856 B2 | 10/2016 | Blomquist | |
| 9,486,571 B2 | 11/2016 | Rosinko | |
| 9,565,718 B2 | 2/2017 | Swanson | |
| 9,737,656 B2 | 8/2017 | Rosinko | |
| 10,279,106 B1 | 5/2019 | Cook et al. | |
| 10,430,043 B2 | 10/2019 | Rosinko et al. | |
| 10,492,141 B2 | 11/2019 | Kruse | |
| 2004/0054263 A1 | 3/2004 | Moerman et al. | |
| 2004/0235446 A1 | 11/2004 | Flaherty et al. | |
| 2007/0060869 A1 | 3/2007 | Tolle et al. | |
| 2007/0060870 A1 | 3/2007 | Tolle et al. | |
| 2007/0093786 A1 | 4/2007 | Goldsmith et al. | |
| 2008/0097912 A1 | 4/2008 | Dicks et al. | |
| 2008/0097917 A1 | 4/2008 | Dicks et al. | |
| 2008/0103554 A1 | 5/2008 | Dicks et al. | |
| 2008/0113292 A1 * | 5/2008 | Matsuo | H01L 51/0013 430/270.1 |
| 2008/0215120 A1 | 9/2008 | Dicks et al. | |
| 2009/0030382 A1 | 1/2009 | Brandt et al. | |
| 2009/0115628 A1 | 5/2009 | Dicks et al. | |
| 2009/0227888 A1 | 9/2009 | Salmi | |
| 2010/0146300 A1 | 6/2010 | Brown | |
| 2010/0305421 A1 | 12/2010 | Ow-Wing | |
| 2011/0034792 A1 | 2/2011 | Williams et al. | |
| 2011/0093285 A1 | 4/2011 | Dicks et al. | |
| 2011/0093286 A1 | 4/2011 | Dicks et al. | |
| 2011/0213621 A1 | 9/2011 | Dicks et al. | |
| 2012/0170521 A1 * | 7/2012 | Vogedes | H04W 76/15 370/329 |
| 2013/0019021 A1 * | 1/2013 | Lau | H04L 67/141 709/227 |
| 2013/0142367 A1 | 6/2013 | Berry | |
| 2013/0324928 A1 | 12/2013 | Kruse | |
| 2014/0297766 A1 * | 10/2014 | Imes | H04L 51/04 709/206 |
| 2014/0323961 A1 | 10/2014 | Blomquist et al. | |
| 2015/0365870 A1 * | 12/2015 | Lauer | H04B 7/18508 370/331 |
| 2016/0212103 A1 * | 7/2016 | Rhoads | G06F 21/604 |
| 2016/0271325 A1 | 9/2016 | Farnan et al. | |
| 2016/0339172 A1 | 11/2016 | Michaud et al. | |
| 2017/0049957 A1 | 2/2017 | Michaud | |
| 2018/0241434 A1 * | 8/2018 | Hayes | A61G 7/018 |
| 2019/0215729 A1 * | 7/2019 | Oyman | H04L 65/80 |
| 2019/0307952 A1 | 10/2019 | Butler et al. | |
| 2019/0321552 A1 | 10/2019 | DiPerna et al. | |
| 2020/0009319 A1 | 1/2020 | Ludolph | |
| 2020/0092192 A1 * | 3/2020 | Ekambaram | H04W 4/70 |
| 2020/0101224 A1 * | 4/2020 | Lintereur | A61M 5/1723 |

* cited by examiner

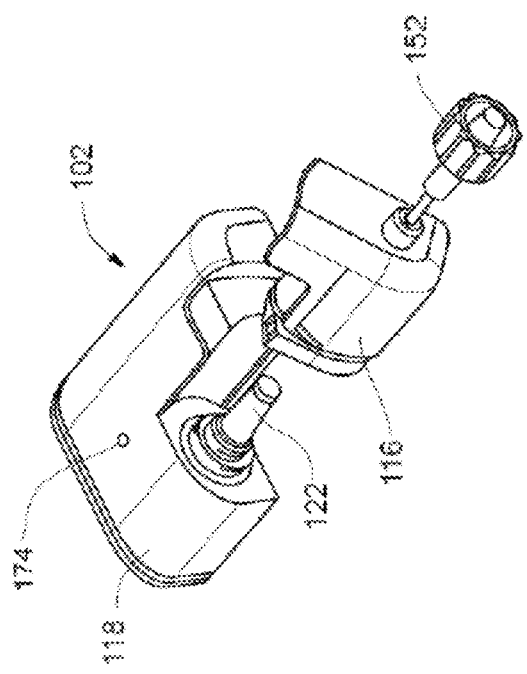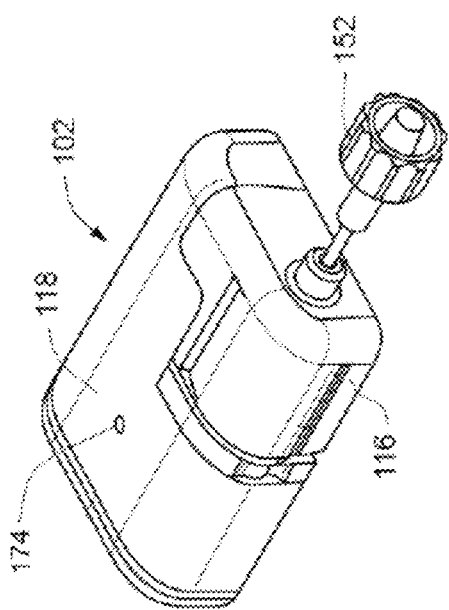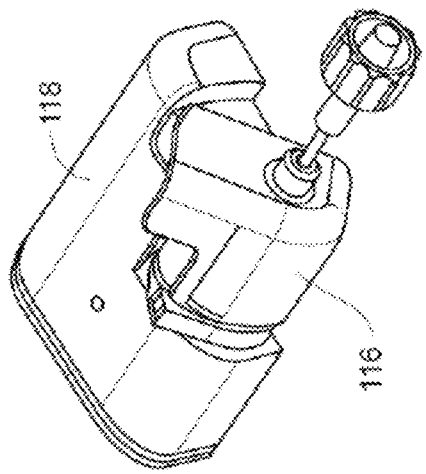

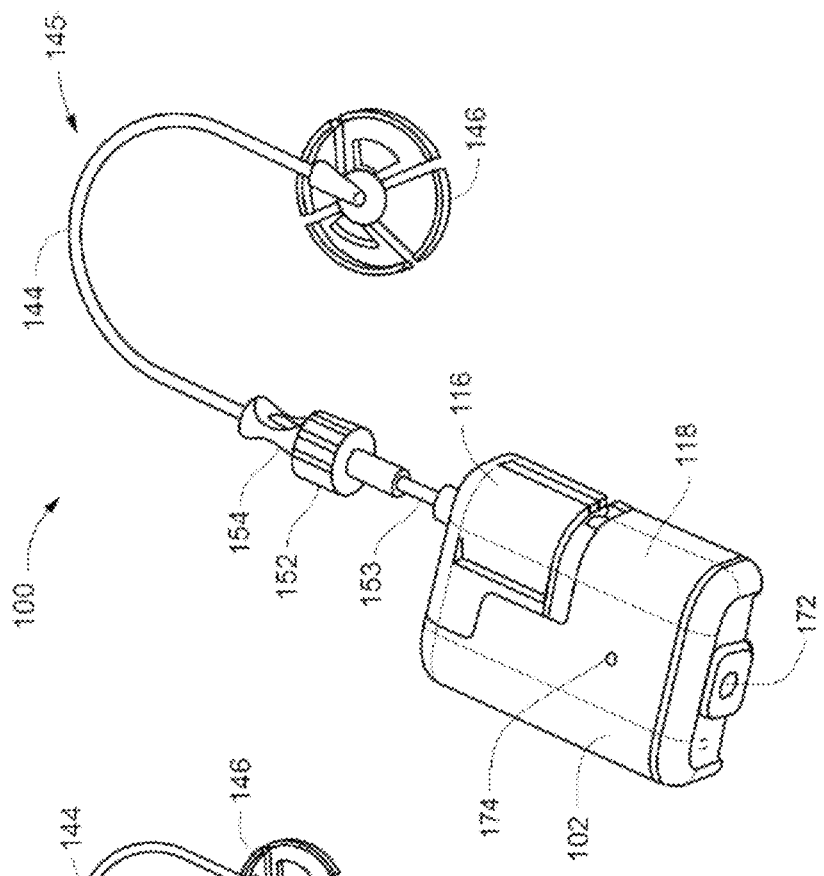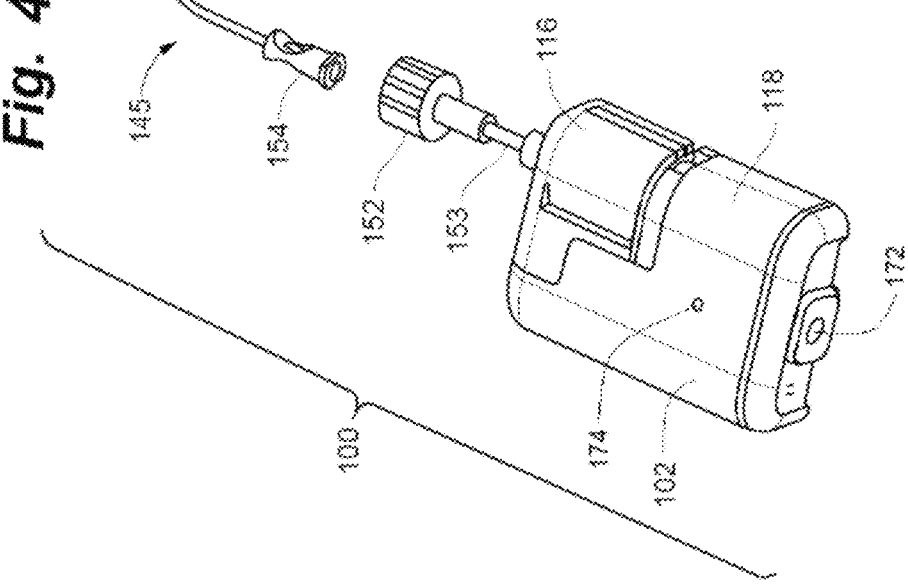

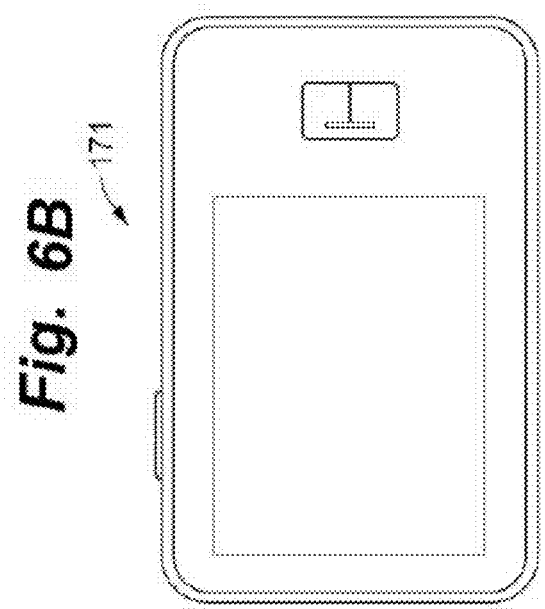
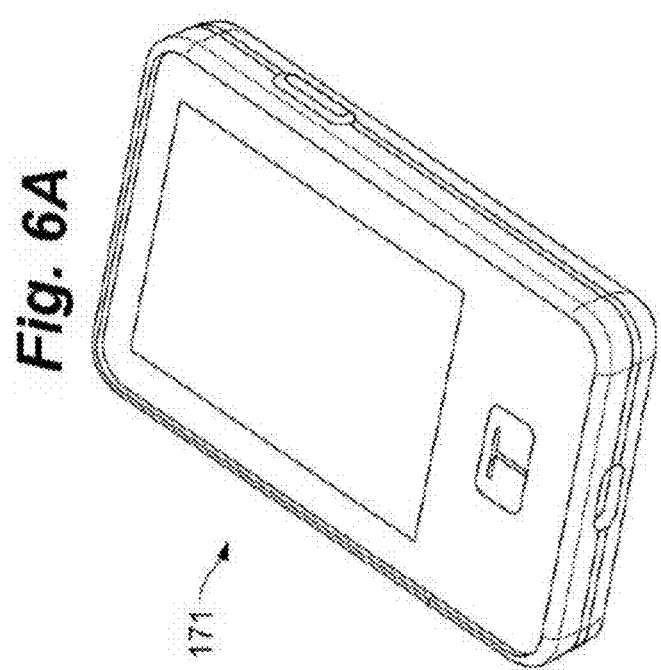

METHODS OF WIRELESS COMMUNICATION IN AN INFUSION PUMP SYSTEM

RELATED APPLICATION

The present application claims the benefit of U.S. Provisional Application No. 62/784,949 filed Dec. 26, 2018, which is hereby incorporated herein in its entirety by reference.

TECHNICAL FIELD

The present invention is directed to portable infusion pumps and more particularly to systems enabling wireless control of infusion pumps.

BACKGROUND

There are a wide variety of medical treatments that include the administration of a therapeutic fluid in precise, known amounts at predetermined intervals. Devices and methods exist that are directed to the delivery of such fluids, which may be liquids or gases, are known in the art.

One category of such fluid delivery devices includes insulin injecting pumps developed for administering insulin to patients afflicted with type I, or in some cases, type II diabetes. Some insulin injecting pumps are configured as portable or ambulatory infusion devices can provide continuous subcutaneous insulin injection and/or infusion therapy as an alternative to multiple daily injections of insulin via a syringe or an insulin pen. Such pumps are worn by the user and may use replaceable cartridges. In some embodiments, these pumps may also deliver medicaments other than, or in addition to, insulin, such as glucagon, pramlintide, and the like. Examples of such pumps and various features associated therewith include those disclosed in U.S. Patent Publication Nos. 2013/0324928 and 2013/0053816 and U.S. Pat. Nos. 8,287,495; 8,573,027; 8,986,253; and 9,381,297, each of which is incorporated herein by reference in its entirety.

Ambulatory infusion pumps have generally been controlled by a user interface provided on the pump. With the proliferation of handheld electronic devices, such as mobile phones (e.g., smartphones), there is a desire to be able to remotely utilize such devices, as well as dedicated wireless controllers designed to work with one or more infusion pumps and/or types of infusion pumps, to optimize usage of infusion pumps. These remote controllers would enable a pump to be monitored, programmed and/or operated more privately, more conveniently and more comfortably. Accordingly, one potential use of dedicated remote devices and handheld consumer electronic devices (such as smartphones, tablets and the like) is to utilize such devices as controllers for remotely programming and/or operating infusion pumps.

However, portable infusion pumps are generally powered by portable batteries and frequent wireless communications with external devices can have a significant effect on infusion pump battery life. In addition to mobile control devices such as smartphones and dedicated remote controllers it may be beneficial to enable infusion pumps to communicate with other devices, such as continuous glucose monitors, glucose meters, and other health monitoring devices, for example. This places further burden on infusion pump battery life. It would therefore be desirable to configure such communications in a manner that reduces the strain on the infusion pump battery and otherwise increase the efficiency of such systems.

SUMMARY

Disclosed herein are methods for establishing communication protocols between wireless devices in infusion pump systems. Infusion pump systems can include a number of components capable of wireless communication with one or more other components including an infusion pump, a continuous glucose monitoring (CGM) system, a smartphone or other multi-purpose consumer electronic device and/or a dedicated remote controller for the infusion pump. Communications among these devices can be coordinated to increase efficiency and conserve battery power.

In embodiments, methods of communication in an infusion pump system in which an infusion pump can communicate with both a smartphone or other multi-purpose consumer electronic device and a dedicated remote controller are coordinated to preserve the pump battery. If only the smartphone or only the remote controller is present in the system at a given time, the device that is present communicates directly with and controls the pump. If the pump, smartphone and remote controller are all present, rather than the smartphone communicating directly with the pump, smartphone communications are instead routed through the remote controller. Similarly, if the smartphone is controlling the pump alone, but then detects that the remote controller has become available for communications, the smartphone will disconnect from the pump and connect to the remote controller to route smartphone communications through the remote controller. This configuration creates more efficient communication and saves battery power because it is difficult for the pump to maintain simultaneous connections to two devices and two connections creates an additional burden on the pump battery. In some configurations, the dedicated remote controller may have full access to program and control the pump while the smartphone has more limited control of pump functionality. In such configurations, routing communications through the remote controller ensures full pump functionality.

In an embodiment, a method of coordinating wireless communications in an infusion pump system including an infusion pump, a multi-purpose consumer electronic device and a dedicated remote controller designed for use with the infusion pump is provided. The infusion pump can be enabled to receive communications from both the multi-purpose consumer electronic device and the dedicated remote controller and carry out operating commands based on the communications. If it is determined that both the multi-purpose consumer electronic device and the dedicated remote controller are available for communication with the infusion pump, communications can be suspended between the infusion pump and the multi-purpose consumer electronic device. Communications generated by the multi-purpose consumer electronic device can then be routed to the dedicated remote controller and transmitted to the infusion pump with the dedicated remote controller. The infusion pump can execute operating commands based on the communications generated by the multi-purpose consumer electronic device after receiving the communications from the dedicated remote controller.

In embodiments, communications between an infusion pump and a continuous glucose monitoring (CGM) system in a system that includes a smartphone or other remote control device can be coordinated to preserve pump battery.

In an infusion pump system in which the pump utilizes data from a CGM system, the CGM system generally sends data to the pump on a periodic, continual basis, such as, for example, every five minutes. This data includes data sent by the pump in making therapy determinations such as data relating to glucose levels and trends of the patient as well as additional data not used by the pump such as diagnostic data relating to the performance of the CGM components. Communications in the system can be configured to separate the CGM data such that the data needed for therapy determinations is sent to the pump, but the diagnostic data that is not used by the pump is instead transmitted directly from the CGM system to the remote control device. Having this data go directly from the CGM to the remote control device lessens the effect of receiving, storing and transmitting the CGM data on the pump battery.

In an embodiment, a method of coordinating wireless communications in an infusion pump system including an infusion pump, a remote control device for remotely controlling the infusion pump, and a continuous glucose monitoring system is provided. Data can be collected with the continuous glucose monitoring system and wireless communication established between the continuous glucose monitoring system and both the infusion pump and the remote control device. The data collected with the continuous glucose monitoring system can be separated into pump data that will be utilized to determine therapy parameters for the infusion pump and non-pump data relating to the continuous glucose monitoring system that are not used to determine therapy parameters for the infusion pump. The pump data can be transmitted to the infusion pump and the non-pump data to the remote control device to conserve battery power of the pump by not requiring the pump to receive, store and later transmit the non-pump data.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which:

FIGS. 3A-3C depicts an embodiment of a pump system according to the disclosure.

FIGS. 4A-4B depict an embodiment of a pump system according to the disclosure.

FIGS. 6A-6B depict remote control devices for a pump system according to embodiments of the disclosure.

Figure 1:
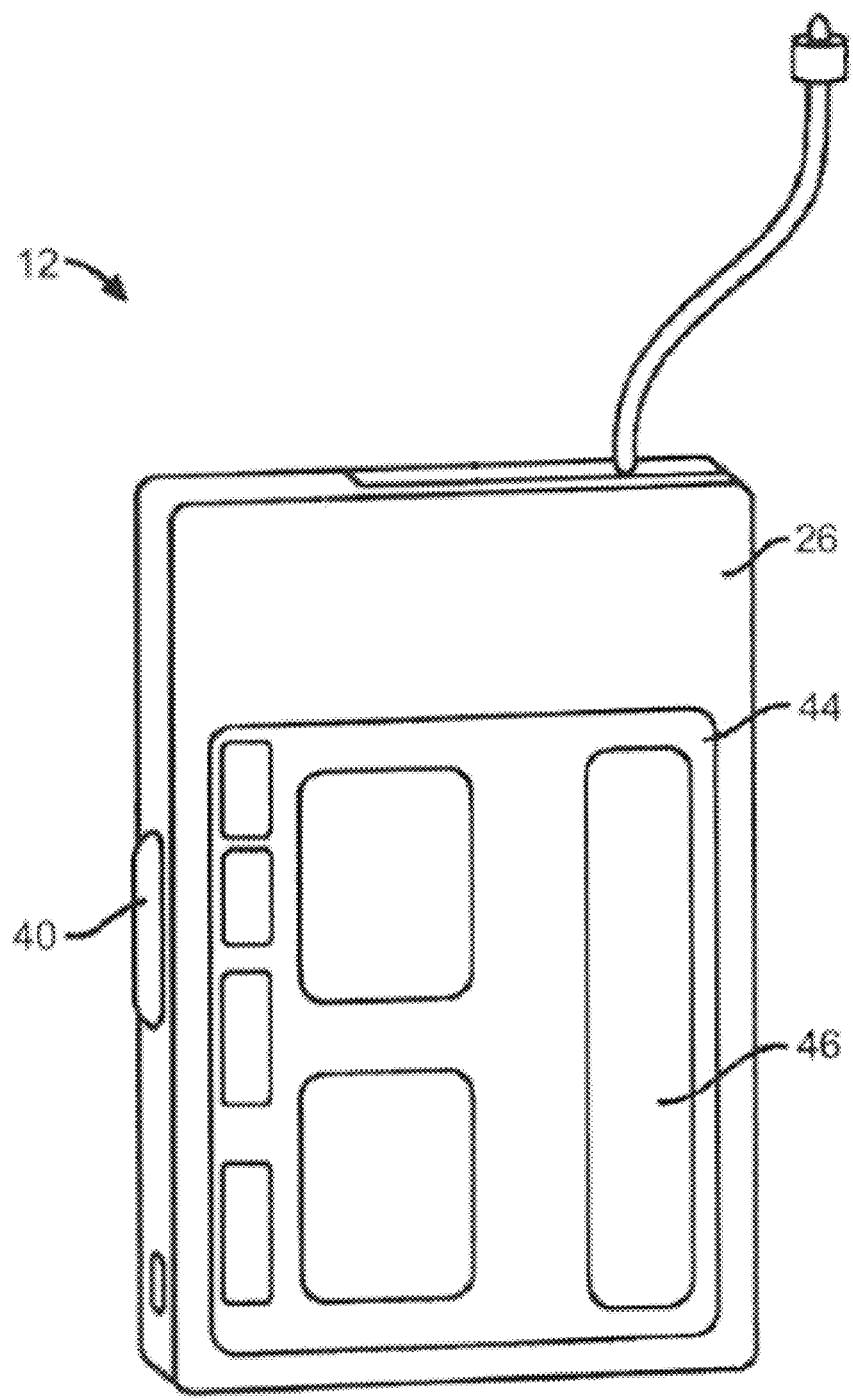
FIG. 1 depicts an embodiment of a pump system according to the disclosure.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

The following detailed description should be read with reference to the drawings in which similar elements in different drawings are numbered the same. The drawings, which are not necessarily to scale, depict illustrative embodiments and are not intended to limit the scope of the invention.

FIG. 1 depicts an exemplary medical device that can be used with embodiments of the disclosure. In this embodiment, the medical device is configured as a pump 12, such as an infusion pump, that can include a pumping or delivery mechanism and reservoir for delivering medicament to a patient and an output/display 44. The type of output/display 44 may vary as may be useful for a particular application. The output/display 44 may include an interactive and/or touch sensitive screen 46 having an input device such as, for example, a touch screen comprising a capacitive screen or a resistive screen. The pump 12 may additionally include a keyboard, microphone, or other input device known in the art for data entry, which may be separate from the display. The pump 12 may also include a capability to operatively couple to one or more blood glucose meters (BGMs) or continuous blood glucose monitors (CGMs) and/or one or more secondary display devices such as a remote display, a remote control device, a laptop computer, personal computer, tablet computer, a mobile communication device such as a smartphone, a wearable electronic watch or electronic health or fitness monitor, or personal digital assistant (PDA), a CGM display etc.

In one embodiment, the medical device can be a portable pump configured to deliver insulin to a patient. Further details regarding such pump devices can be found in U.S. Pat. No. 8,287,495, which is incorporated herein by reference in its entirety. In other embodiments, the medical device can be an infusion pump configured to deliver one or more additional or other medicaments to a patient.

Figure 2:
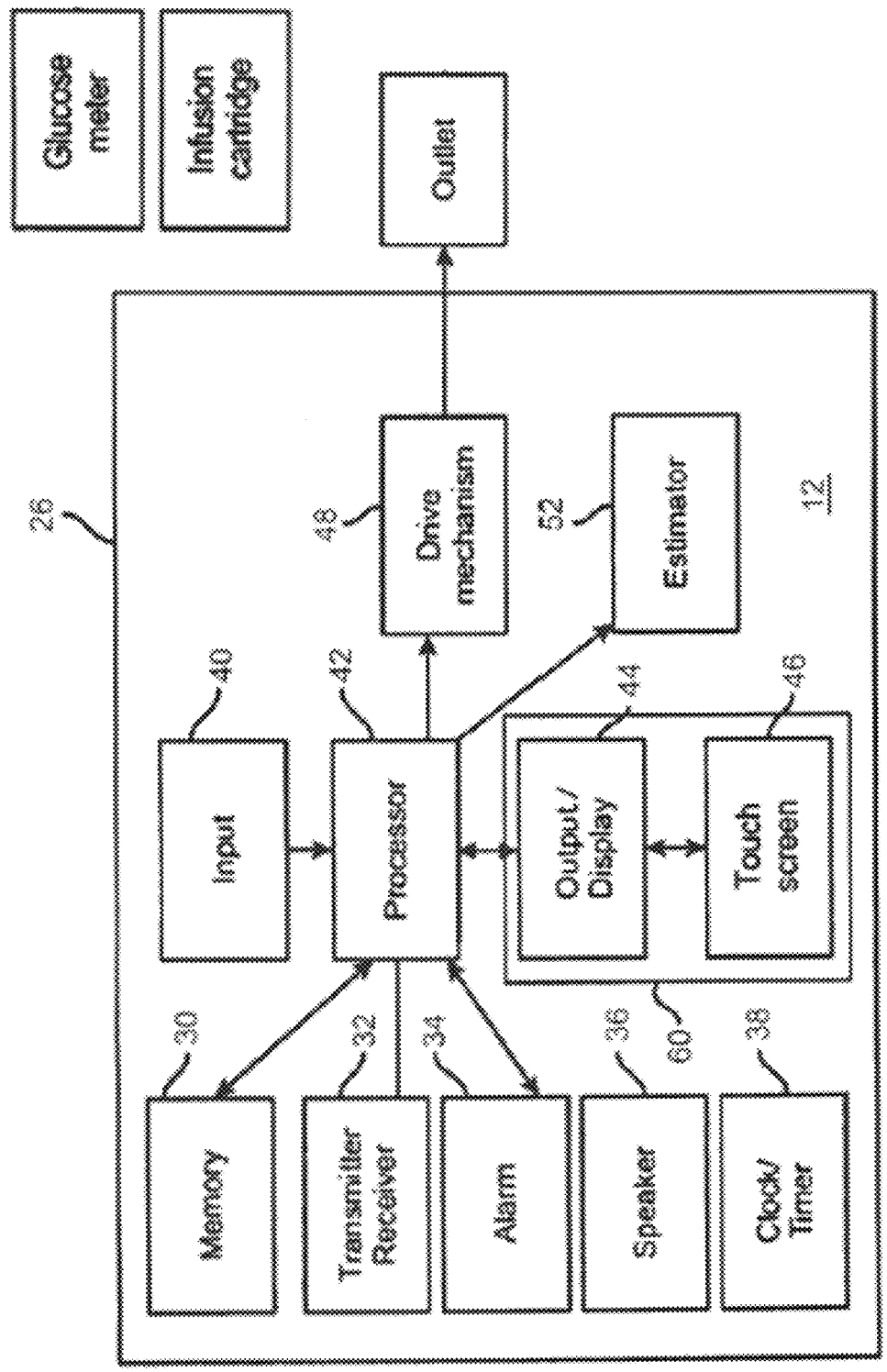
FIG. 2 depicts a block diagram representing an embodiment of a pump system according to the disclosure.

FIG. 2 illustrates a block diagram of some of the features that can be used with embodiments, including features that may be incorporated within the housing 26 of a medical device such as a pump 12. The pump 12 can include a processor 42 that controls the overall functions of the device. The infusion pump 12 may also include, e.g., a memory device 30, a transmitter/receiver 32, an alarm 34, a speaker 36, a clock/timer 38, an input device 40, a user interface suitable for accepting input and commands from a user such as a caregiver or patient, a drive mechanism 48, an estimator device 52 and a microphone (not pictured). One embodiment of a user interface as shown in FIG. 2 is a graphical user interface (GUI) 60 having a touch sensitive screen 46 with input capability. In some embodiments, the processor 42 may communicate with one or more other processors within the pump 12 and/or one or more processors of other devices, for example, a continuous glucose monitor (CGM), display device, smartphone, etc. through the transmitter/receiver. The processor 42 may also include programming that may allow the processor to receive signals and/or other data from one or more input devices, such as sensors that may sense pressure, temperature and/or other parameters.

FIGS. 3A-3C depict another pump system including a pump 102 that can be used with embodiments. Drive unit 118 of pump 102 includes a drive mechanism 122 that mates with a recess in disposable cartridge 116 of pump 102 to attach the cartridge 116 to the drive unit 118 and provide for delivery of medicament such as insulin from the cartridge 116 to a user through a cannula. Further details regarding such pumps can be found in U.S. patent application Ser. No. 14/707,851 filed May 8, 2015 and U.S. Patent Publication Nos. 2016/0339172 and 2017/0049957, each of which is hereby incorporated herein by reference in its entirety.

In one embodiment, pump 102 includes a processor that controls operations of the pump and, in some embodiments, may receive commands from a separate device for control of operations of the pump. Such a separate device can include, for example, a dedicated remote control or a smartphone or other consumer electronic device executing an application configured to enable the device to transmit operating commands to the processor of pump 102. In some embodiments, processor can also transmit information to one or more separate devices, such as information pertaining to device parameters, alarms, reminders, pump status, etc. In one embodiment pump 102 does not include a display but may include one or more indicator lights 174 and/or one or more input buttons 172. Pump 102 can also incorporate any or all of the features described with respect to pump 12 in FIG. 2.

Figure 5:
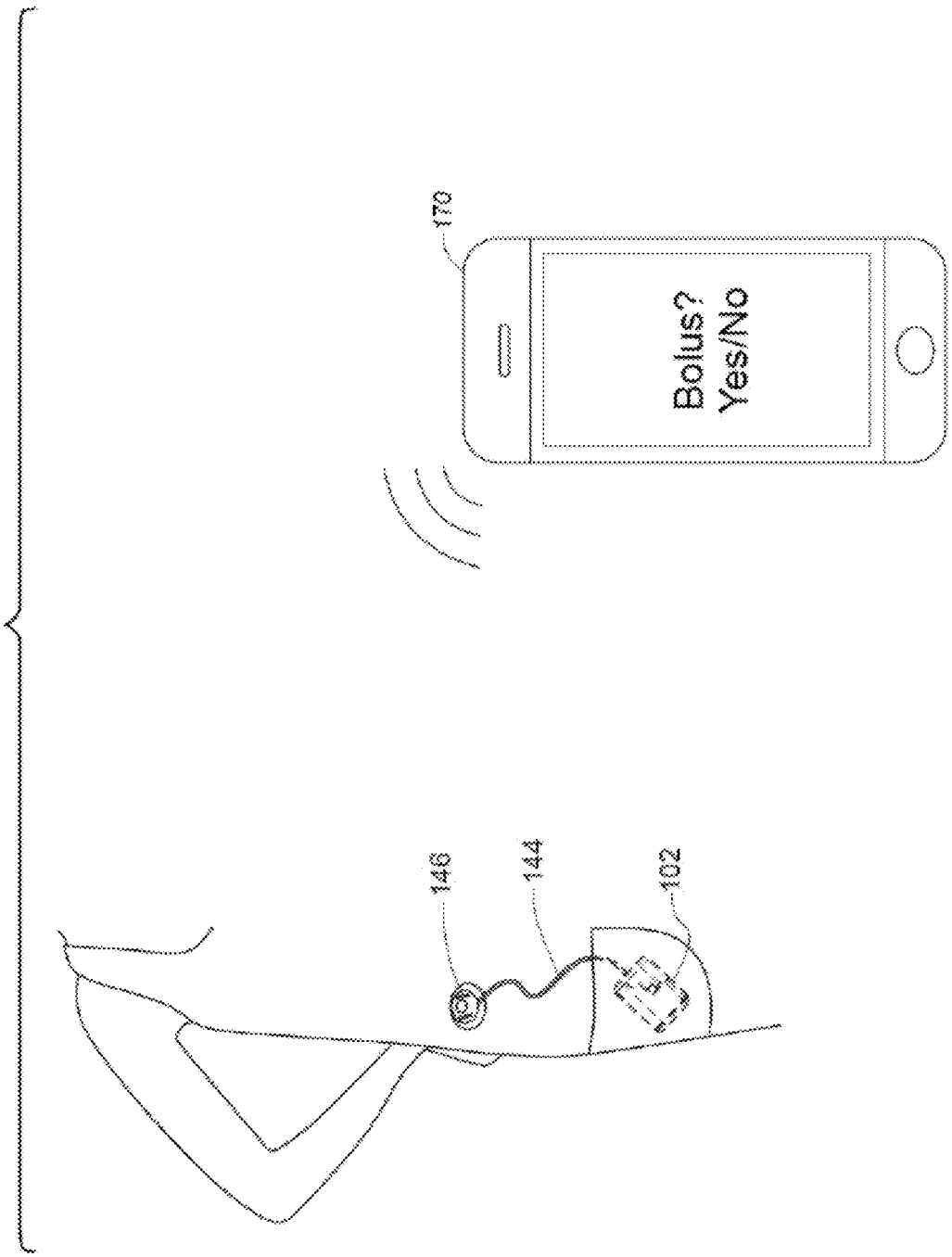
FIG. 5 depicts an embodiment of a pump system according to the disclosure.

As depicted in the embodiment of FIGS. 4A-4B, pump system 100 can include a pump 102 and an infusion set 145. FIG. 4A depicts this infusion set 145 as not connected to pump while FIG. 4B depicts infusion set 145 connected to pump 102 via connectors 154 and 152 and tubing 153. Infusion set 145 can include tubing 144 extending between a connector 154 and a site connector 146. Connector 154 can be configured to couple to pump 102 at connector 152 extending from tubing 153. Site connector 146 can be configured to be attached to an infusion site on a user, while pump 102 can be carried in a separate location, such as the user's pocket (as depicted in FIG. 5) or another location on the user's body. Various lengths of tubing 144 can be used in this embodiment to accommodate the user's preference.

Referring to FIGS. 5-6B, one or more remote control devices 170, 171 can be used to communicate with the processor of pump 12 and/or pump 102 to control delivery of medicament and transfer data with pump via a wired or a wireless electromagnetic signal, such as via, e.g., a near field communication (NFC) radio frequency (RF) modality or other RF modalities such as Bluetooth®, Bluetooth® low energy, mobile or Wi-Fi communication protocols, for example, according to embodiments of the present disclosure. Such a remote control can include, for example, a mobile communication device 170, such as a smart phone (as depicted in FIG. 5) executing a software application for control of the pump, a dedicated remote controller 171 (as depicted in FIGS. 6A-6B), a wearable electronic watch or electronic health or fitness monitor or personal digital assistant (PDA), etc., or a tablet, laptop or personal computer. Such communications between (and among) the one or more remote control devices 170, 171 and pump 102 may be one-way or two-way for, e.g., effective transfer of data among the devices and the pump, control of pump operations, updating software on the devices and/or pump, and allowing pump-related data to be viewed on the devices and/or pump.

Figure 7:
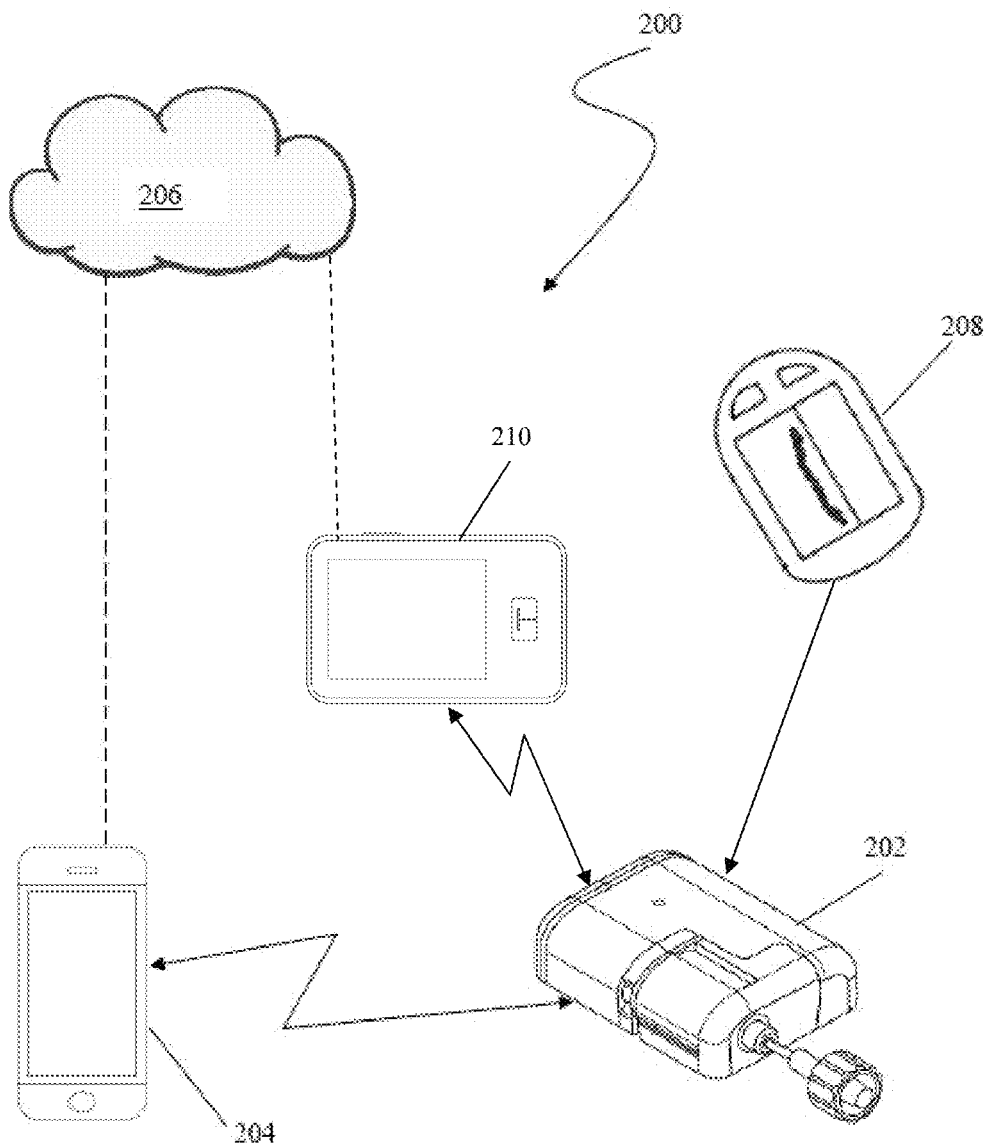
FIG. 7 depicts a schematic representation of a pump system according to an embodiment of the disclosure.

FIG. 7 depicts various components of a pump system 200 according to an embodiment. System components can include, for example, a user-wearable infusion pump 202, a smartphone or other multi-purpose consumer electronic device 204, remote data storage 206 such as the cloud, one or more optional peripheral devices such as a continuous glucose monitor 208, and a dedicated remote controller 210. In the depicted embodiment, the smartphone 204 and/or the dedicated remote controller 210 can obtain data and information from the cloud, such as a medicament delivery control algorithm and communicate control commands and/or information to the infusion pump 202 and receive data and information from the infusion pump 202. As depicted in FIG. 7, the pump 202 can be capable of unidirectional or bidirectional communications via, for example, Bluetooth, with both the remote controller 210 and the smartphone 204. The pump 202 can in various embodiments communicate with a continuous glucose monitor 208 with a corresponding sensor and/or can directly communicate with the CGM sensor. Other optional peripheral devices that can communicate with the pump 202, the smartphone 204 and/or the dedicated remote control device 210 include for example, one or more of a blood glucose meter or other analyte sensing device, an activity or other health monitor, etc.

Although depicted with the multi-purpose consumer electronic device 204 being a smartphone, in various embodiments the consumer electronic device can alternatively or additional include one or more of a wearable electronic watch, electronic health or fitness monitor, personal digital assistant (PDA), or a tablet, laptop or personal computer, etc. A multi-purpose consumer electronic device can be any device sold to consumers and used for a variety of functions and which can be configured or programmed to communicate with and/or control an infusion pump as one of said functions. In some embodiments, systems as described herein may include more than one multi-purpose consumer electronic device configured for communication with the infusion pump (e.g., a smartphone and an electronic watch).

As noted above, systems 200 (such as the system depicted by way of example in FIG. 7) can include both a dedicated remote controller 210 and a smartphone 204 or other multi-purpose consumer electronic device operating an application capable of communicating with and sending one or more control commands to the pump 202. For example, in some embodiments the smartphone may be provided with a limited set of features and/or commands, such as, for example, display only capability with no control functions, the ability to program and issue bolus commands but no other control commands to the pump, etc., whereas the remote control device may be enabled for full programming and control of all pump functions.

One concern in systems 200 (such as the system depicted by way of example in FIG. 7) is that the multiple communication options for the pump can lead to an excessive drain of the pump's rechargeable battery and inefficient and/or redundant communications. The present application therefore provides novel communication methods that can aid in reducing the battery drain on a pump while still providing all the advantages of such an integrated communication system.

Figure 8:
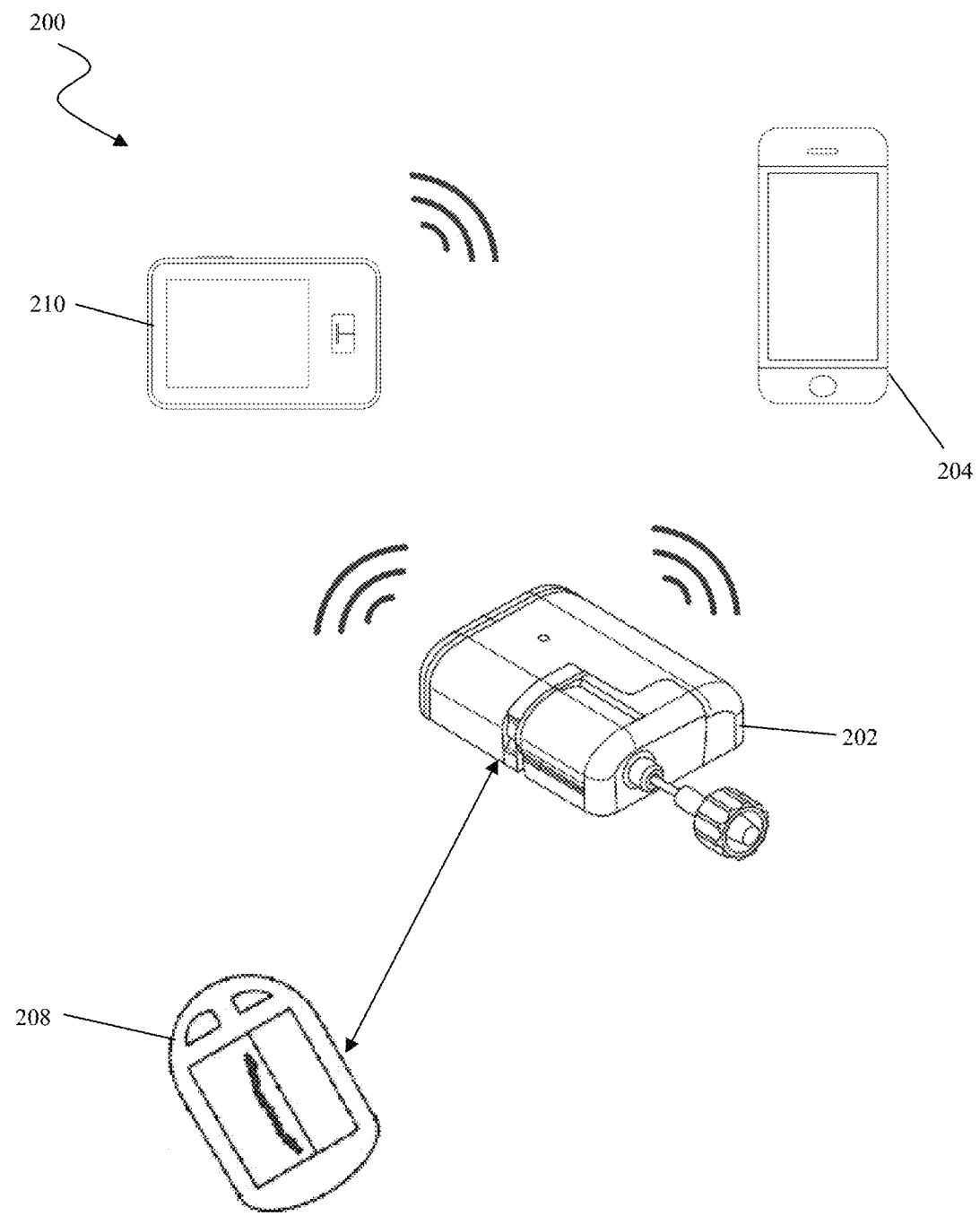
FIG. 8 depicts a schematic representation of a pump system according to an embodiment of the disclosure.

FIG. 8 depicts a schematic representation of an infusion pump system 200 including infusion pump 202, smartphone 204 or other remote consumer electronic device, dedicated remote controller 210 and continuous glucose monitoring system 208. As noted above, pump 202 can receive glucose information from the CGM system 208 and control commands from both the smartphone 204 and the remote controller 210. Pump 202 can also send communications to these devices. In embodiments, the devices communicate using Bluetooth. In the depicted embodiment, pump 202 is generally regularly communicating with the CGM system 208 on a periodic basis and is continuously or periodically broadcasting an advertising packet for detection by the phone 204 and the remote controller 210 when not already connected to these devices. Note that although the pump 202 is depicted as communicating with a monitoring device of the CGM system 208, the pump can alternatively or additionally communicate directly with the glucose sensor and transmitter of the CGM system. The remote 210 is also advertising for detection by the phone 204. The phone 204 is always looking to detect the pump 202 and the remote 210, which helps conserve the overall battery power of the system because the phone will generally have the largest battery.

Figure 9A:
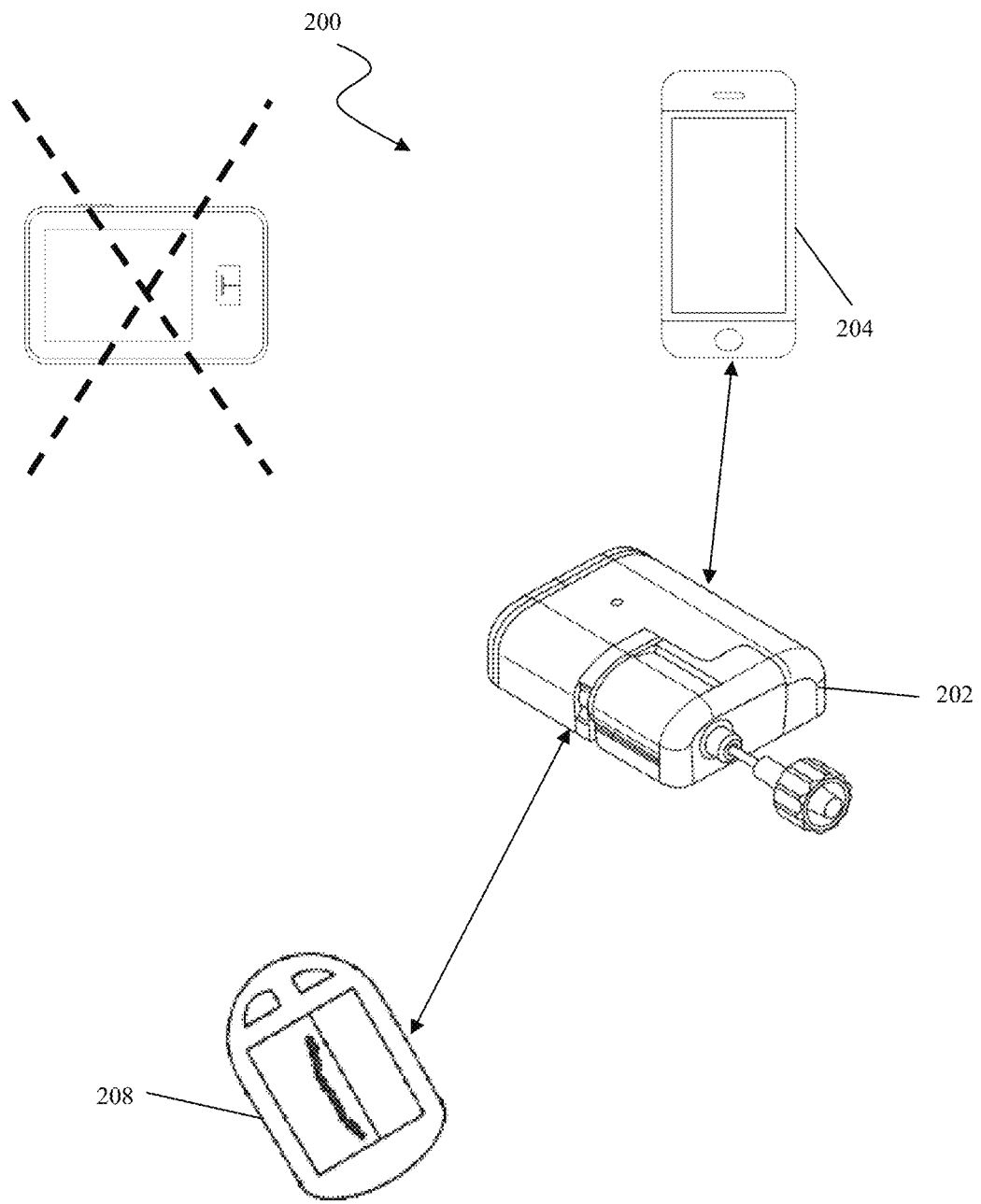
FIGS. 9A-9C depict schematic representations of a pump system according to an embodiment of the disclosure.
Figure 9B:
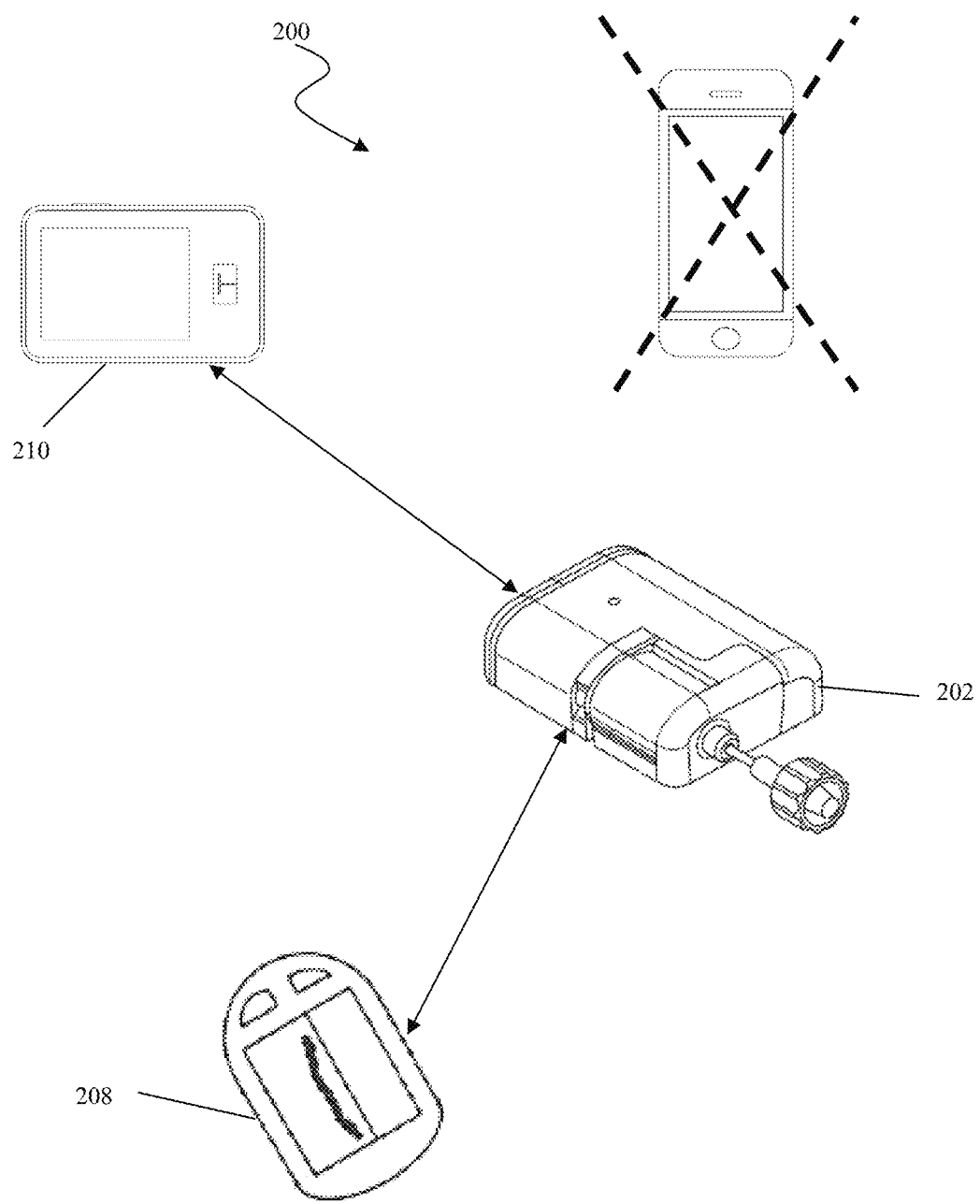
Figure 9C:
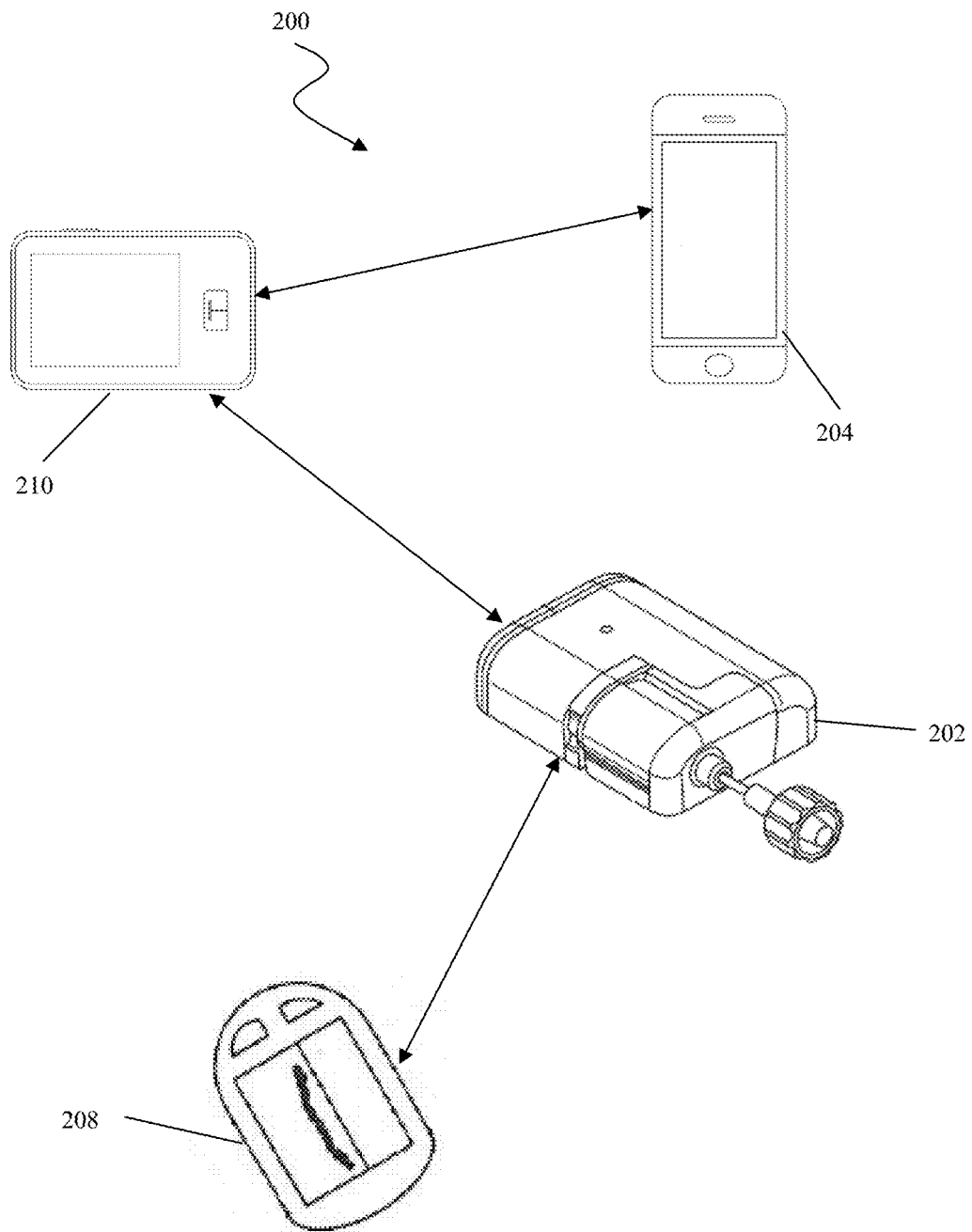

FIGS. 9A-9C schematically depict various communications modalities depending on which elements of system 200 are present. In FIG. 9A, the phone 204 has detected the pump 202 but not the remote controller 210, so the phone 204 communicates directly with the pump. In FIG. 9B, the remote controller 210 has detected the pump 202 but the phone 204 is not present such that it has not established a connection with either of the other devices, so the remote controller 210 communicates directly with the pump 202.

In FIG. 9C, both the phone 204 and the remote controller are present 210. In this situation, rather than the pump 202 communicating with both the controller 210 and the phone 204, communications generated by the phone 204 are relayed through the controller 210 to the pump 202. The system is configured in this manner because it can be difficult for the pump 202 to maintain two simultaneous connections with the two control devices for stable and efficient communications and having two simultaneous connections causes a greater burden on the pump battery and therefore drains the battery faster. In an embodiment such as described above in which the phone may be limited to certain control functions, routing the communications through the pump enables availability of all functions of the pump as the phone may not be able to transmit certain communications generated by the controller to the pump. In addition to prolonging the use of the pump between charges, preserving battery power of the pump provides the additional benefit of limiting the risk of losing connectivity between the pump 202 and the CGM system 208 that may be used in making therapy determinations due to the pump losing power.

Referring again to FIG. 9A in which the remote controller 210 is not present, if the phone 204 subsequently detects the controller 210, the phone 204 will disconnect from the pump 202 and connect to the controller 210 to route communications through the controller 210 as depicted in FIG. 9C. In alternative embodiments, particularly in embodiments where the phone has full control of the pump, communications could instead be routed through the phone.

Figure 10:
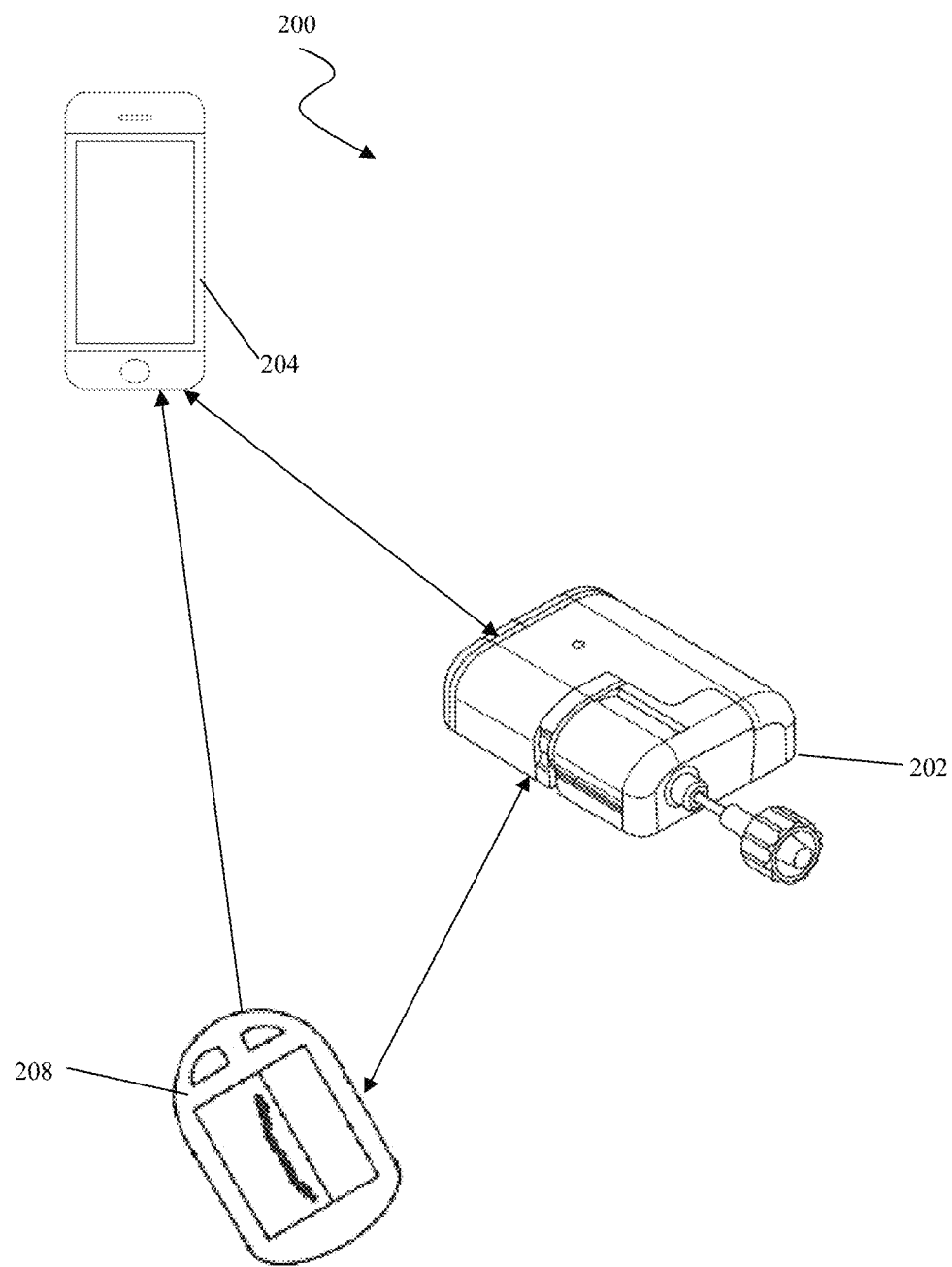
FIG. 10 depicts a schematic representation of a pump system according to an embodiment of the disclosure.

As shown and described above with respect to system 200, pump 202 is generally continually in communication with CGM system 208 to receive information pertaining to glucose levels and other data. For example, the CGM system 208 may provide data every five minutes to the pump 202. While some of this data such as estimated glucose levels and related data is critical to the functioning of the pump 202 and proper therapy determinations, the data provided by the CGM system includes other data, such as diagnostic data relating to the performance of the CGM sensor and transmitter that is not used by the pump. This data is instead stored in pump memory and later sent from the pump to another device such as a software management system. Requiring the pump to receive, store, and later transmit this additional data that is not utilized by the pump presents another unnecessary drain on the pump battery. Such data can include, for example, one or more of sensor and transmitter performance and diagnostic information, various voltage levels, resistance values, battery voltage, temperature data, current data, sensor noise data, radio connectivity logs, wireless quality of service metrics, connectivity history, error messages, alarm/alert history, sensor-transmitter disconnection logging, and/or analysis of any of the above FIG. 10 depicts a system that addresses the foregoing issue by limiting the data in the communications sent from the CGM system 208 to the pump 202. As can be seen in FIG. 10, system 200 can be configured such that the CGM system 208 communicates with both the pump 202 and a smartphone 204 or other remote consumer electronic device. In the depicted configuration, the CGM system 208 will send only glucose level data and other therapy-relevant data required by the pump to enable proper therapy determinations. Other data, such as diagnostic data of the CGM system is instead sent to the phone 204. This more limited data sent to the phone 204 helps preserve the battery power of the pump 202. In addition, the additional data sent to the phone 204 does not have to be sent as frequently as the therapy related data sent to the pump 202 and could be sent, e.g., every 2-3 hours, twice a day, once a day, etc., which would also help preserve the batteries of the other devices. In other embodiments, the CGM system 208 can communicate with a dedicated remote controller 210 instead of or in addition to the smartphone 204.

Although the embodiments herein have been specifically described with respect to an ambulatory infusion pump, the inventions disclosed herein could be employed with any other type of programmable medical device capable of receiving and executing remote commands. Such devices include, for example, implantable pumps, defibrillators, spinal cord stimulation systems, etc. Embodiments could further include non-medical applications.

Although the infusion pump embodiments herein are specifically described primarily with respect to the delivery of insulin, delivery of other medicaments, singly or in combination with one another or with insulin, including, for example, glucagon, pramlintide, etc., as well as other applications are also contemplated. Device and method embodiments discussed herein may be used for pain medication, chemotherapy, iron chelation, immunoglobulin treatment, dextrose or saline IV delivery, treatment of various conditions including, e.g., pulmonary hypertension, or any other suitable indication or application. Non-medical applications are also contemplated.

Also incorporated herein by reference in their entirety are commonly owned U.S. Pat. Nos. 6,999,854; 8,133,197; 8,287,495; 8,408,421 8,448,824; 8,573,027; 8,650,937; 8,986,523; 9,173,998; 9,180,242; 9,180,243; 9,238,100; 9,242,043; 9,335,910; 9,381,271; 9,421,329; 9,486,171; 9,486,571; 9,492,608; 9,503,526; 9,555,186; 9,565,718; 9,603,995; 9,669,160; 9,715,327; 9,737,656; 9,750,871; 9,867,937; 9,867,953; 9,940,441; 9,993,595; 10,016,561; 10,201,656; 10,279,105; 10,279,106; 10,279,107; 10,357,603; 10,357,606; 10,492,141. commonly owned U.S. Patent Publication Nos. 2009/0287180; 2012/0123230; 2013/0053816; 2014/0276423; 2014/0276569; 2014/0276570; 2017/0182248; 2017/0250971; 2018/0021514; 2018/0071454; 2019/0240398; 2019/0307952; and 2019/0365997 and commonly owned U.S. patent application Ser. Nos. 16/507,146 and 16/598,343.

Further incorporated by reference herein in their entirety are U.S. Pat. Nos. 8,601,465; 8,502,662; 8,452,953; 8,451, 230; 8,449,523; 8,444,595; 8,343,092; 8,285,328; 8,126,728; 8,117,481; 8,095,123; 7,999,674; 7,819,843; 7,782,192; 7,109,878; 6,997,920; 6,979,326; 6,936,029; 6,872,200; 6,813,519; 6,641,533; 6,554,798; 6,551,276; 6,295,506; and 5,665,065.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

For purposes of interpreting the claims, it is expressly intended that the provisions of 35 U.S.C. § 112(f) are not to be invoked unless the specific terms "means for" or "step for" are recited in a claim.

The invention claimed is:

1. A method of coordinating wireless communications in an infusion pump system including an infusion pump, a multi-purpose consumer electronic device and a dedicated remote controller designed for use with the infusion pump, comprising:

enabling the infusion pump to receive communications from both the multi-purpose consumer electronic device and the dedicated remote controller and carry out operating commands based on the communications;

determining if both the multi-purpose consumer electronic device and the dedicated remote controller are available for communication with the infusion pump;

suspending communications between the infusion pump and the multi-purpose consumer electronic device if both the multi-purpose consumer electronic device and the dedicated remote controller are available for communication with the infusion pump;

routing communications generated by the multi-purpose consumer electronic device to the dedicated remote controller after suspending communications between the infusion pump and the multi-purpose consumer electronic device;

transmitting the communications routed from the multi-purpose consumer electronic device to the dedicated remote controller to the infusion pump with the dedicated remote controller; and causing the infusion pump to execute operating commands based on the communications generated by the multi-purpose consumer electronic device after receiving the communications from the dedicated remote controller.

2. The method of claim 1, further comprising reinitiating communications between the multi-purpose consumer electronic device and the infusion pump if it is determined that the dedicated remote controller has become unavailable for communication with the infusion pump.

3. The method of claim 1, further comprising transmitting communications generated by the dedicated remote control device to the infusion pump and causing the infusion pump to execute operating commands based on the communications generated by the dedicated remote controller.

4. The method of claim 1, wherein the multi-purpose consumer electronic device is provided with reduced functionality for control of the infusion pump relative to the dedicated remote controller.

5. The method of claim 1, further comprising enabling the infusion pump to receive communications including glucose level readings measured by a continuous glucose sensor.

6. The method of claim 1, wherein the infusion pump is enabled to receive the communications via Bluetooth.

7. The method of claim 1, wherein the multi-purpose consumer electronic device is a smartphone.

8. The method of claim 1, wherein the multi-purpose consumer electronic device is an electronic watch.

9. The method of claim 1, wherein determining if both the multi-purpose consumer electronic device and the dedicated remote controller are available for communication with the infusion pump includes the multi-purpose consumer electronic device detecting a presence of both the infusion pump and the dedicated remote controller.

10. The method of claim 1, further comprising routing communications generated by the infusion pump to the dedicated remote controller after suspending communications between the infusion pump and the multi-purpose consumer electronic device.

* * * * *